US011557788B2

(12) United States Patent
Mohtadi et al.

(10) Patent No.: US 11,557,788 B2
(45) Date of Patent: Jan. 17, 2023

(54) PREPARATION OF IONIC LIQUIDS BASED ON BORON CLUSTERS

(71) Applicants: Toyota Motor Engineering & Manufacturing North America, Inc., Plano, TX (US); Monash University, Clayton (AU)

(72) Inventors: Rana Mohtadi, Northville, MI (US); Oscar Tutusaus, Ann Arbor, MI (US); Douglas R. MacFarlane, Clayton (AU); Mega Kar, Beaconsfield (AU)

(73) Assignees: Toyota Motor Engineering & Manufacturing North America, Inc., Plano, TX (US); Monash University, Clayton (AU)

( * ) Notice: Subject to any disclaimer, the term of this patent is extended or adjusted under 35 U.S.C. 154(b) by 197 days.

(21) Appl. No.: 15/930,711

(22) Filed: May 13, 2020

(65) Prior Publication Data

US 2020/0274188 A1    Aug. 27, 2020

Related U.S. Application Data

(62) Division of application No. 15/702,997, filed on Sep. 13, 2017, now Pat. No. 10,673,095.

(51) Int. Cl.
*H01M 10/05* (2010.01)
*H01M 10/056* (2010.01)
(Continued)

(52) U.S. Cl.
CPC ......... *H01M 10/056* (2013.01); *C07C 217/08* (2013.01); *C07F 5/02* (2013.01);
(Continued)

(58) Field of Classification Search
None
See application file for complete search history.

(56) References Cited

U.S. PATENT DOCUMENTS

| 9,455,473 B1 | 9/2016 | Mohtadi et al. |
| 2013/0034780 A1 | 2/2013 | Muldoon |

(Continued)

FOREIGN PATENT DOCUMENTS

| CN | 102584878 A | 7/2012 | |
| CN | 103641751 A | 3/2014 | |
| EP | 1874784 B1 * | 8/2009 | ............. B01F 17/00 |

OTHER PUBLICATIONS

Hosmane, N.S., Boron Science, New Technologies and Applications, CRC Press 2011, Print ISBN: 978-1-4398-2662-1.
(Continued)

*Primary Examiner* — Ula C Ruddock
*Assistant Examiner* — Tony S Chuo
(74) *Attorney, Agent, or Firm* — Christopher G. Darrow; Darrow Mustafa PC

(57) ABSTRACT

Electrolytes and electrochemical cells include a novel ionic liquid having a quaternary cation and a boron cluster anion. In some versions, the boron cluster anion will be a functionalized or unfunctionalized icosahedral boranyl or carboranyl anion. Electrochemical cells have an electrolyte including the ionic liquid. In some versions, the ionic liquid is used as a solvent to dissolve an ionic shuttle salt for transport of active material, with an optional co-solvent. Methods to synthesize the ionic liquid include contacting a boron cluster salt with a quaternary salt to form the ionic liquid by a metathesis reaction.

16 Claims, 13 Drawing Sheets

(51) Int. Cl.
| | |
|---|---|
| C07F 5/02 | (2006.01) |
| C07C 217/08 | (2006.01) |
| H01M 10/0568 | (2010.01) |
| H01M 10/054 | (2010.01) |
| H01M 10/0525 | (2010.01) |

(52) U.S. Cl.
CPC ..... *H01M 10/054* (2013.01); *H01M 10/0525* (2013.01); *H01M 10/0568* (2013.01); *H01M 2300/0045* (2013.01)

(56) References Cited

U.S. PATENT DOCUMENTS

| | | | |
|---|---|---|---|
| 2014/0034917 | A1 | 2/2014 | Mohtadi et al. |
| 2014/0038037 | A1 | 2/2014 | Mohtadi et al. |
| 2014/0038061 | A1 | 2/2014 | Mohtadi et al. |
| 2014/0349178 | A1 | 11/2014 | Mohtadi et al. |
| 2014/0349199 | A1 | 11/2014 | Mohtadi et al. |
| 2015/0311565 | A1 | 10/2015 | Muldoon |
| 2015/0325881 | A1 | 11/2015 | Mohtadi |

OTHER PUBLICATIONS

Tutusaus, O. et al., "Paving the Way towards Highly Stable and Practical Electrolytes for Rechargeable Magnesium Batteries", ChemElectroChem, 2(1), pp. 51-57 (2015).
Carter, T. J. et al., "Boron Clusters as Highly Stable Magnesium-Battery Electrolytes", Angewandte Chemie International Edition, 126, pp. 3237-3241, pp. 51-57 (2014).
Dymon, J. et al., "Designing ionic liquids with boron cluster anions: alkylpyridinium and imidazolium [nido-C2B9H11] and [closo-CB11H12] carborane salts," Dalton Trans., pp. 2999-3006 (2008).
Kar, M. et al., Ionic liquid electrolytes for reversible magnesium electrochemistry, Chem. Comm, 52, pp. 4033-4036 (2016).
Larsen, A. et al., Designing Ionic Liquids: Imidazolium Melts with Inert Carborane Anions, J. Am. Chem. Soc., 122, pp. 7264-7272 (2000).
Jenne, C. et al., Alkoxy substituted halogenated closododecaborates as anions for ionic liquids, Dalton Trans., 44, pp. 13119-13124 (2015).
Zhou N., et al., Investigations on a series of novel ionic liquids containing the [closo-B12Cl12]22 dianion, RSC Advances, 2, pp. 9830-9838 (2012).
Liu, S. et al., Carborane-Derivatized Low-Melting Salts with Ether-Functionalized Cations—Preparation and Properties, Euro. J. Inorg. Chem., pp. 1910-1920 (2011).
Guo, Y. et al., "Boron-based electrolyte solutions with wide electrochemical windows for rechargeable magnesium batteries," Energy Environ. Sci., vol. 5, pp. 9100-9106 (2012).
Muldoon, J. et al., "Electrolyte roadblocks to a magnesium rechargeable battery,", Energy Environ. Sci., 5, pp. 5941-5950 (2012).
Nieuwenhuyzen, M. et al., "Ionic Liquids Containing Boron Cluster Anions," Inorg. Chem., vol. 48, pp. 889-901 (2009).
Yoo, H.D. et al., "Mg rechargeable batteries: an on-going challenge," Energy Environ. Sci., 6, pp. 2265-2279 (2013).
Mohtadi, R. et al., "Magnesium batteries: Current state of the art, issues and future perspectives," Beilstein J. Nanotechnol. 5, pp. 1291-1311 (2014).
Mohtadi, R. et al., "Magnesium Borohydride: From Hydrogen Storage to Magnesium Battery," Angewandte Chemie International Edition, 51(39) (2012).
Tutusaus, O. et al., "An Efficient Halogen-Free Electrolyte for Use in Rechargeable Magnesium Batteries," Angew. Chem., 127, pp. 8011-8015 (2015).
MacFarlane, D., et al., "Energy applications of ionic liquids," Energy Environ. Sci., vol. 7, No. 1, pp. 232-250 (2014).
Kar, M., "Ether functionalized ionic liquids for rechargeable batteries," Thesis (2015).

\* cited by examiner

PREPARATION OF IONIC LIQUIDS BASED ON BORON CLUSTERS

CROSS-REFERENCE TO RELATED APPLICATIONS

The present application is a Divisional of U.S. patent application Ser. No. 15/702,997, filed Sep. 13, 2017, incorporated herein by reference in its entirety.

TECHNICAL FIELD

The present disclosure generally relates to ionic liquids and, more particularly, to ionic liquids as components of electrolytes for electrochemical cells.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Ionic liquids are promising candidates as electrolyte solvents in electrochemical cells, in part due to their negligible volatility. As such, ionic liquids can be particularly useful as electrolyte components in high temperature applications.

Accordingly, it would be desirable to provide new ionic liquids with good dissociation properties and ionic conductivity, as well as convenient methods to make them.

SUMMARY

This section provides a general summary of the disclosure, and is not a comprehensive disclosure of its full scope or all of its features.

In various aspects, the present teachings provide an electrolyte composition. The electrolyte composition includes an ionic liquid having a formula $A_pQ$. A is a quaternary ammonium or phosphonium cation with four side chains, $R_1$, $R_2$, $R_3$, and $R_4$, wherein each of $R_1$, $R_2$, $R_3$, and $R_4$ is, independently selected from a group consisting of C2-C12 alkyl, and poly(ethylene glycol) methyl ether having from 1-20 ethylene glycol subunits. Q is a boron cluster anion, and p is one or two.

In other aspects, the present teachings provide an electrochemical cell. The cell includes an anode that contains a reduced form of an active material when at least partially charged; a cathode; and an electrolyte mediating ionic communication between the anode and the cathode. The electrolyte includes an ionic liquid having a formula $A_pQ$. A is a quaternary ammonium or phosphonium cation with four side chains $R_1$, $R_2$, $R_3$, and $R_4$, wherein each of $R_1$, $R_2$, $R_3$, and $R_4$ is, independently selected from a group consisting of C2-C12 alkyl, and poly(ethylene glycol) methyl ether having from 1-20 ethylene glycol subunits. Q is a boron cluster anion, and p is one or two.

In still other aspects, the present teachings provide a method for synthesizing an ionic liquid. The method includes a step of contacting a quaternary ammonium or phosphonium salt with a boron cluster salt to form the ionic liquid via a salt metathesis reaction. The method can additionally include a step of purifying the ionic liquid by at least one method selected from: contacting the ionic liquid with an adsorbent; contacting the ionic liquid with a highly water-reactive metal; and placing the ionic liquid under vacuum at a temperature up to 100° C.

Further areas of applicability and various methods of enhancing the above ionic liquid technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein.

It should be noted that the figures set forth herein are intended to exemplify the general characteristics of the methods, algorithms, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures.

DETAILED DESCRIPTION

The present teachings provide novel ionic liquids useful as electrolyte components in Li-ion, Mg, Na, and other electrochemical cells, as well as methods of preparing the ionic liquids. The ionic liquids of the present teachings can facilitate the preparation of non-volatile electrolyte compositions, and have surprisingly low melting temperatures and excellent dissociation properties, supporting high ionic conductivity of such electrolytes.

Figure 1A:
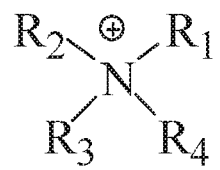
FIG. 1A is a line drawing of a generic quaternary ammonium cation, having side chains $R_1$, $R_2$, $R_3$, and $R_4$.
Figure 1B:
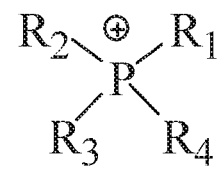
FIG. 1B is a line drawing of a generic quaternary phosphonium cation, having side chains $R_1$, $R_2$, $R_3$, and $R_4$.
Figure 1C:
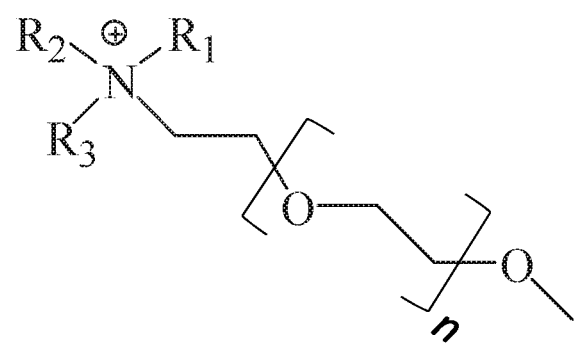
FIG. 1C is a line drawing of a quaternary cation of the type shown in FIG. 1A, and having at least one poly (ethylene glycol) methyl ether side chain.
Figure 1D:
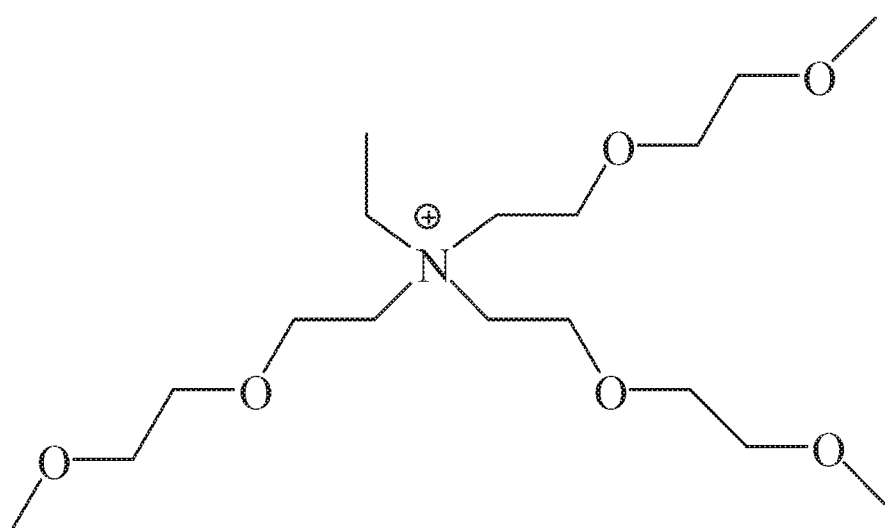
FIG. 1D is a line drawing of a disclosed quaternary cation, N-ethyl-N,N,N-tris[2-(2-methoxyethoxy)ethyl]ammonium.
Figure 1E:
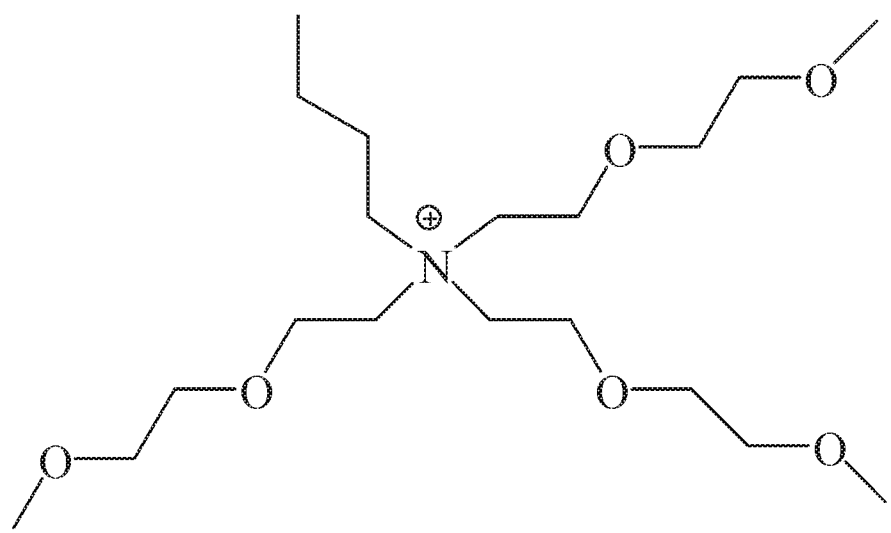
FIG. 1E is a line drawing of another disclosed quaternary cation, N-butyl-N,N,N-tris[2-(2-methoxyethoxy)ethyl]ammonium.

The ionic liquids of the present teachings include at least one quaternary cation and at least one boron cluster anion, including boranyl and carboranyl anions. The preparation methods include a metathesis reaction between a quaternary salt of a suitable ammonium cation and a boron cluster salt An ionic liquid useful as an electrolyte solvent in an electrochemical cell is disclosed. The ionic liquid has a quaternary cation and a boron cluster anion. The ionic liquid can have a formula $A_pQ$ where A is the quaternary cation, Q is the boron cluster anion, and p is either one or two. The quaternary cation can be an ammonium or phosphonium cation having four side chains, $R_1$, $R_2$, $R_3$, and $R_4$, as shown in FIGS. 1A and 1B, respectively. In some implementations, $R_1$, $R_2$, $R_3$, and $R_4$ can each, independently, be: a C2-C12 alkyl; or a poly(ethylene glycol) methyl ether having from 1-20 ethylene glycol subunits. In some implementations, the quaternary cation can have a structure as shown in FIG. 1C, in which at least one side chain is a poly(ethylene glycol) methyl ether having from 1-20 ethylene glycol subunits (i.e. where n is an integer from 1 through 20, inclusive), and $R_2$, $R_3$, and $R_4$ is each, independently: a C2-C12 alkyl; or a poly(ethylene glycol) methyl ether having from 1-20 ethylene glycol subunits. In some specific implementations, the quaternary cation can be at least one of N-ethyl-N,N,N-tris[2-(2-methoxyethoxy)ethyl]ammonium, shown in FIG. 1D, and N-butyl-N,N,N-tris[2-(2-methoxyethoxy)ethyl]ammonium, shown in FIG. 1E. N-ethyl-N,N,N-tris[2-(2-methoxyethoxy)ethyl]ammonium cation will alternatively be referred to hereinafter as $[N_{2(2O2O1)(2O2O1)(2O2O1)}]^+$, and N-butyl-N,N,N-tris[2-(2-methoxyethoxy)ethyl]ammonium cation will alternatively be referred to hereinafter as $[N_{4(2O2O1)(2O2O1)(2O2O1)}]^+$.

In some implementations, the boron cluster anion can be an anion having any formula of:

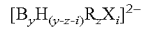 Anion Formula I,

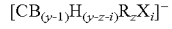 Anion Formula II,

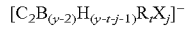 Anion Formula III,

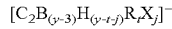 Anion Formula IV, or

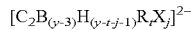 Anion Formula V, wherein y is an integer within a range of 6 to 12; (z+i) is an integer within a range of 0 to y; (t+j) is an integer within a range of 0 to (y−1); and X is F, Cl, Br, I, or a combination thereof. Substituent R as included in Anion Formulae I-IV is an organic substituent belonging to any of: group (i) a linear, branched-chain, or cyclic C1-C18 alkyl, perfluoroalkyl, or partially fluorinated alkyl group; group (ii) a C6-C14 aryl, perfluoroaryl, or partially fluorinated aryl group; group (iii) a linear, branched-chain, or cyclic C1-C18 alkoxy, perfluoroalkoxy, or partially fluorinated alkoxy group; group (iv) a C6-C14 aryloxy, perfluoroaryloxy, or partially fluorinated aryloxy group, and group (v) a substituent that includes two or more moieties as defined by any two or more of groups (i)-(iv). Non-limiting examples of group (v) substituents include a benzyl, methoxyethyl, or trifluoromethoxyethyl group.

It is to be understood that when z or t is greater than one (i.e. when a plurality of R groups is present in the boron cluster anion), the plurality of R groups can include individual substituents selected from a plurality of groups (i)-(v). This can alternatively be stated as follows: when R of any of Anion Formulae I-V defines a plurality of substituents, the plurality of substituents can comprise a plurality of groups (i)-(v). For example, a boron cluster anion can simultaneously include both an alkyl group and a partially fluorinated aryloxy group.

Similarly, where it is noted above that X can be F, Cl, Br, I, or a combination thereof, this indicates that when i is an integer within a range of 2 to y, or j is an integer within a range of 2 to (y−1), this indicates that a plurality of halogen substituents is present. In such a situation, the plurality of halogen substituents can include F, Cl, Br, I, or any combination thereof. For example, a boron cluster anion having three halogen substituents (i.e. where i or j equals 3), the three halogen substituents could be three fluorine substituents; 1 chlorine substituent, 1 bromine substituent, and 1 iodine substituent; or any other combination.

The expression "partially fluorinated" as used herein in the terms "partially fluorinated alkyl", "partially fluorinated aryl", "partially fluorinated alkoxy", and "partially fluorinated aryloxy" indicates that the group contains at least one carbon-fluorine bond. Non-limiting examples of suitable alkyl groups include methyl, ethyl, propyl, isopropyl, butyl, tert-butyl, cyclohexyl, and any other linear, branched-chain, or cyclic C1-C18 alkyl group. Non-limiting examples of suitable aryl groups include phenyl, naphthyl, and anthracenyl.

It is to be understood that when p equals two, the two organic cations contained in the stoichiometric unit of the organic ionic liquid can be the same cation or can be two different cations.

Figure 2A:
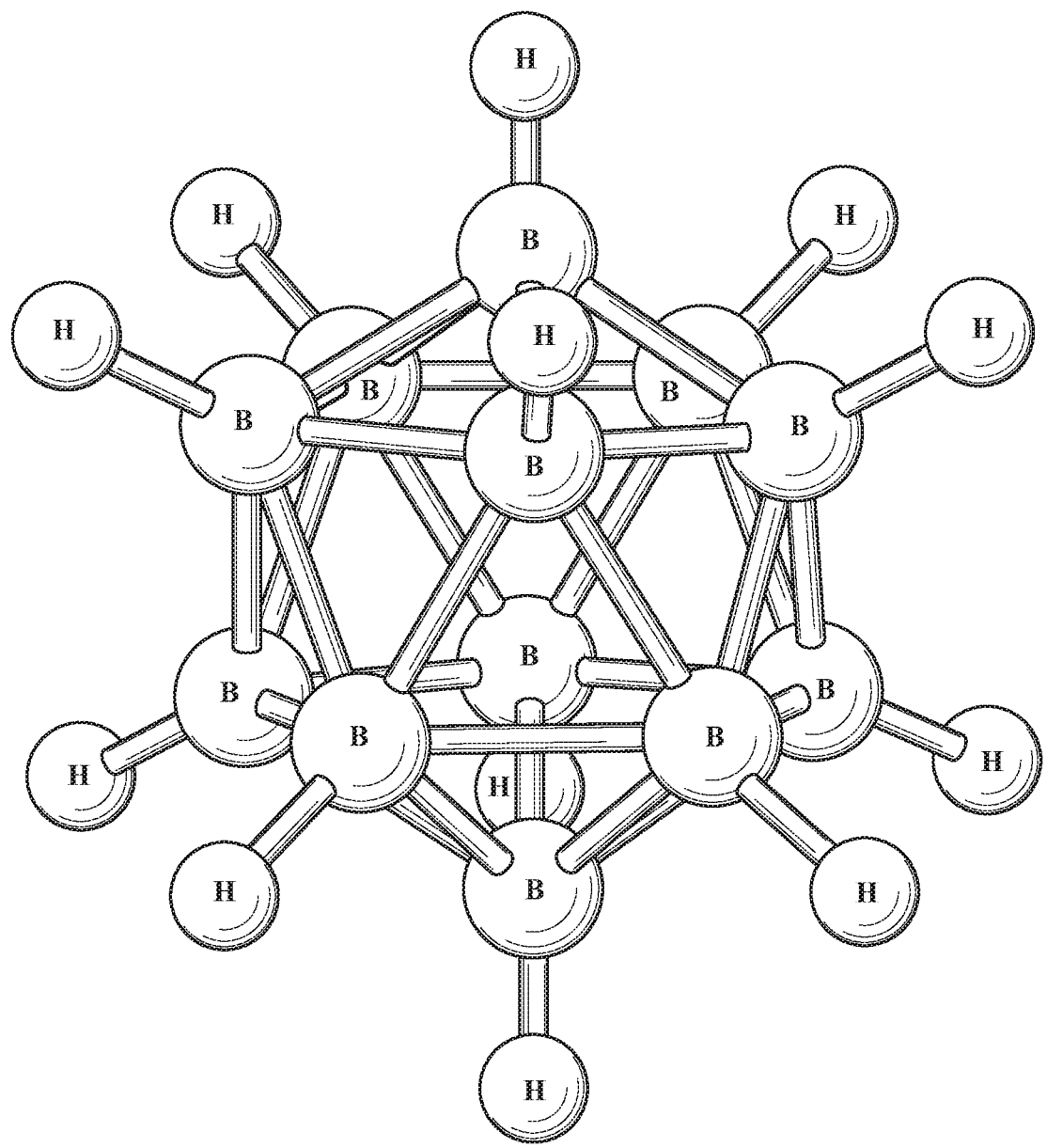
FIG. 2A is a ball-and-stick drawing of a boron cluster anion of the present disclosure, closo-$[B_{12}H_{12}]^{2-}$.
Figure 2B:
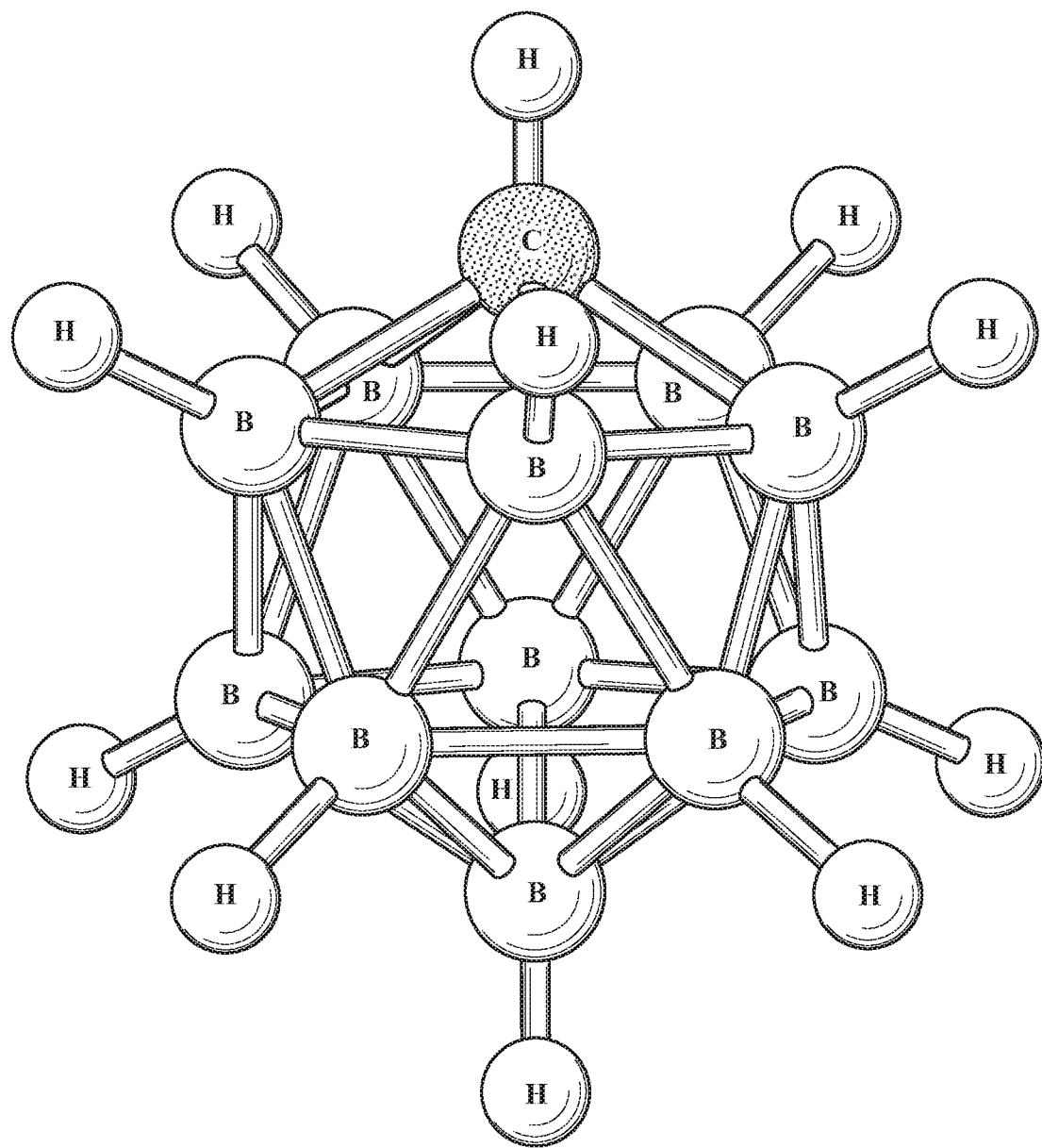
FIG. 2B is a ball-and-stick drawing of another boron cluster anion of the present disclosure, closo-$[CB_{11}H_{12}]^{-}$.
Figure 2C:
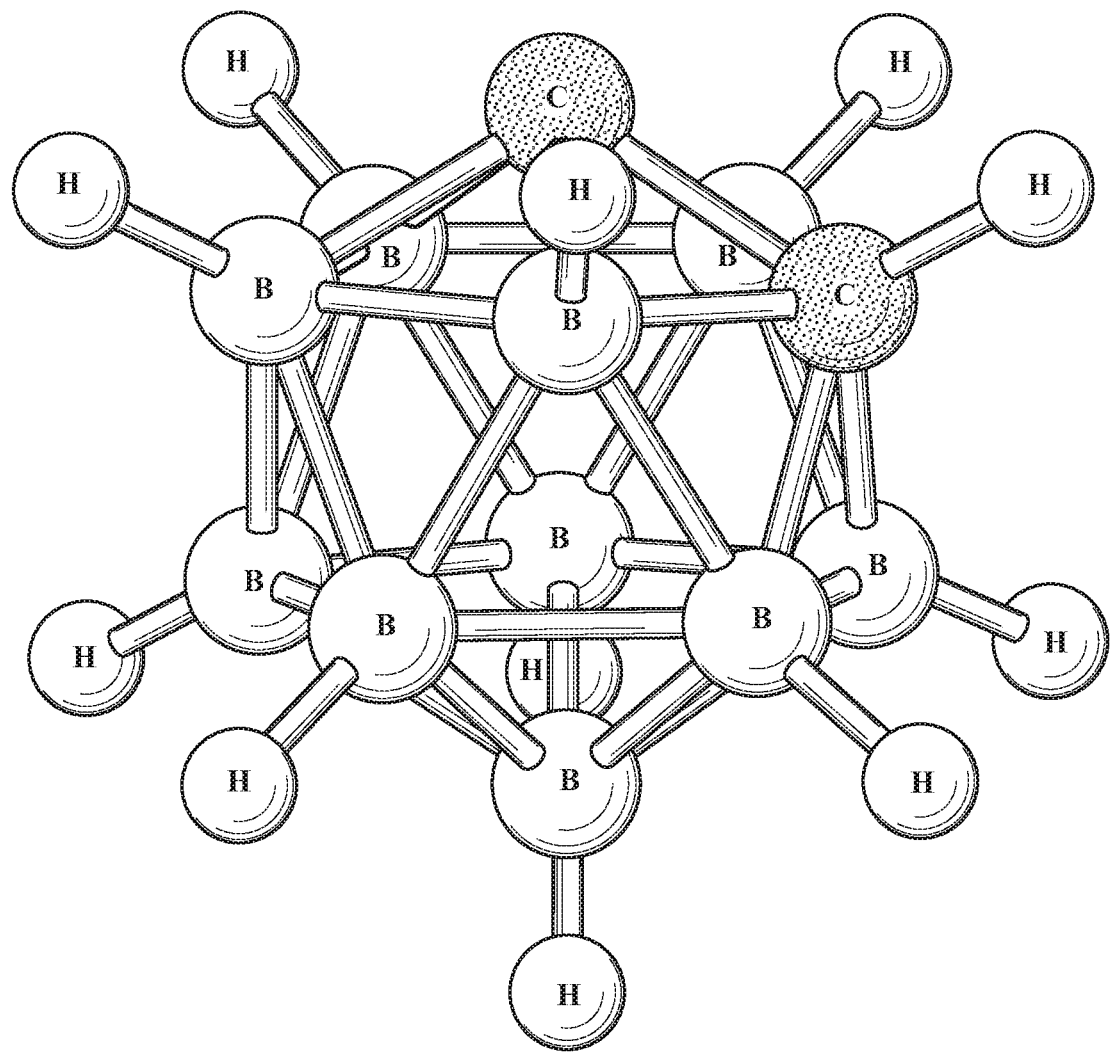
FIG. 2C is a ball-and-stick drawing of yet another boron cluster anion of the present disclosure, closo-$[C_2B_{10}H_{11}]^{-}$.
Figure 2D:
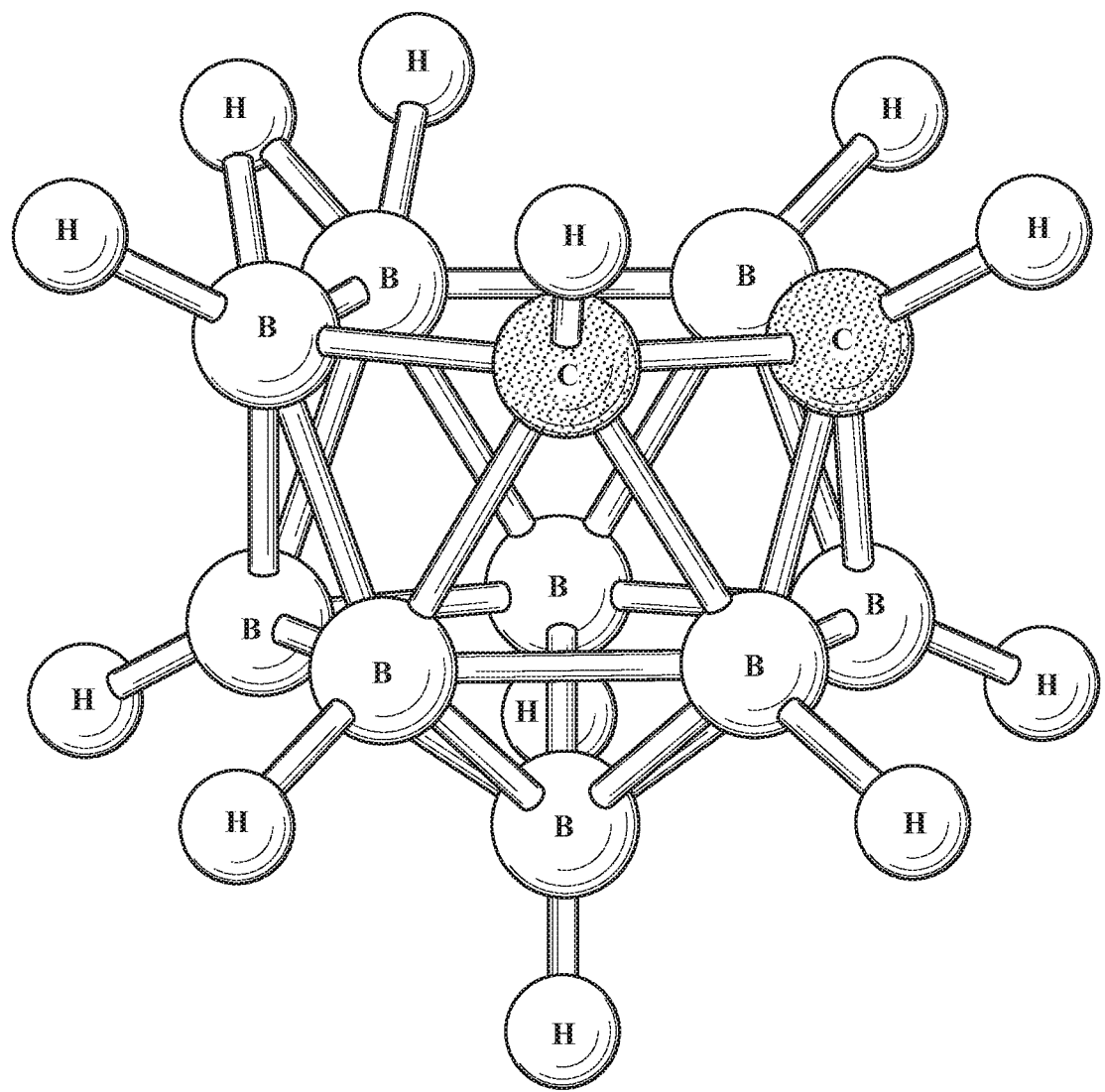
FIG. 2D is a ball-and-stick drawing of yet another boron cluster anion of the present disclosure, nido-$[C_2B_9H_{12}]^{-}$.
Figure 2E:
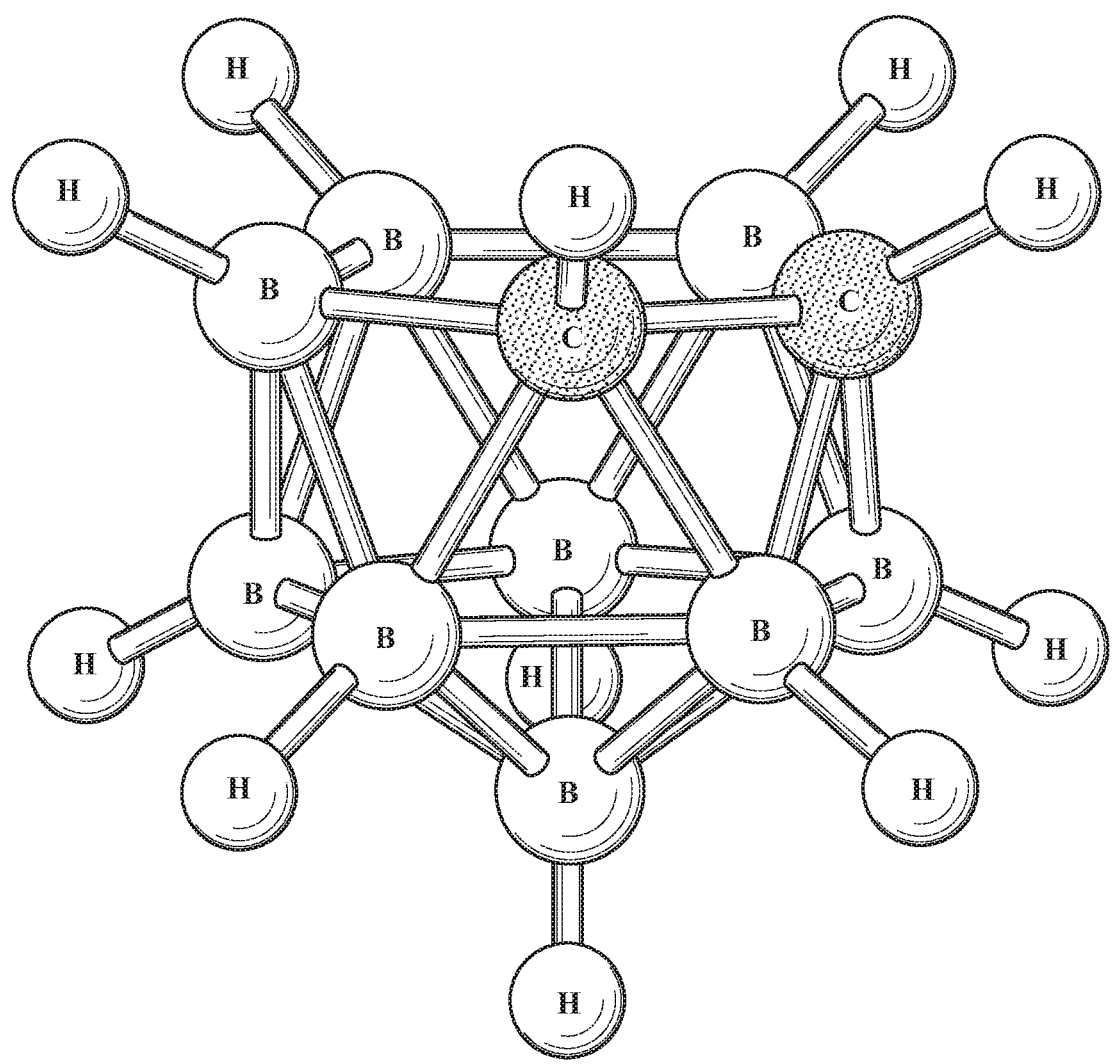
FIG. 2E is a ball-and-stick drawing of yet another boron cluster anion of the present disclosure, nido-$[C_2B_9H_{11}]^{2-}$.

In different implementations, the boron cluster anion can include any of a substituted or unsubstituted closo- and nido-boron cluster anion. In some implementations, the boron cluster anion will be a closo-boron cluster anion, such as closo-$[B_6H_6]^{2-}$, closo-$[B_{12}H_{12}]^{2-}$, closo-$[CB_{11}H_{12}]^-$, or closo-$[C_2B_{10}H_{11}]^-$. In some implementations, the boron cluster anion will be a nido-boron cluster anion, such as nido-$[C_2B_9H_{12}]^-$. In many implementations, the boron cluster anion will be an icosahedral boron cluster anion. Exemplary icosahedral, closo-boron cluster anions closo-$[B_{12}H_{12}]^{2-}$, closo-$[CB_{11}H_{12}]^-$, or closo-$[C_2B_{10}H_{11}]^-$ are shown schematically as ball-and-stick drawings in FIGS. 2A-2C, respectively. Exemplary nido-boron cluster anions, nido-$[C_2B_9H_{12}]^-$ and nido-$[C_2B_9H_{11}]^{2-}$ are shown schematically as ball-and-stick drawings in FIGS. 2D and 2E, respectively.

Figure 3:
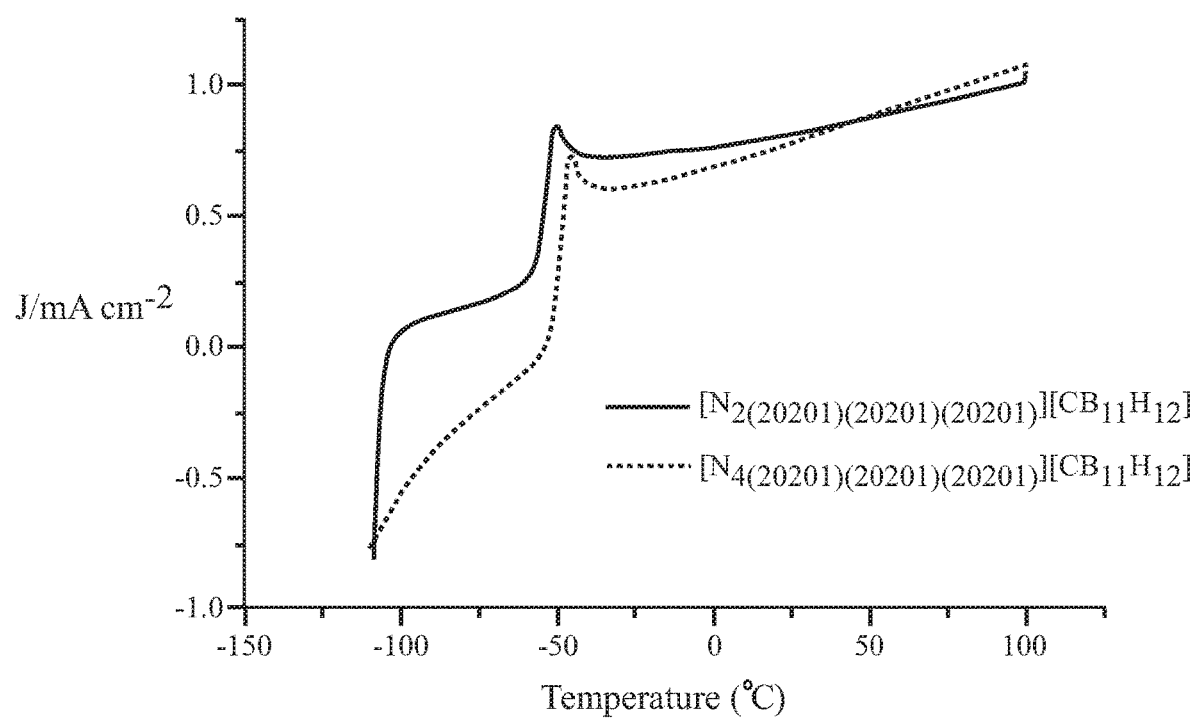
FIG. 3 is a plot of Differential Scanning calorimetry (DSC) data for an ionic liquid having the anion of FIG. 2B and the cation of FIG. 1D or 1E.

It is observed that the disclosed ionic liquids have unusually low melting temperatures. FIG. 3A shows a plot of Differential Scanning calorimetry (DSC) data for the ionic liquids $[N_{2(2O2O1)(2O2O1)(2O2O1)}][CB_{11}H_{12}]$(solid line) and $[N_{4(2O2O1)(2O2O1)(2O2O1)}][CB_{11}H_{12}]$(dashed line). The results show that both ionic liquids have melting transitions at about −50° C.; specifically, −52° C. and −47° C., respectively.

Figure 4:
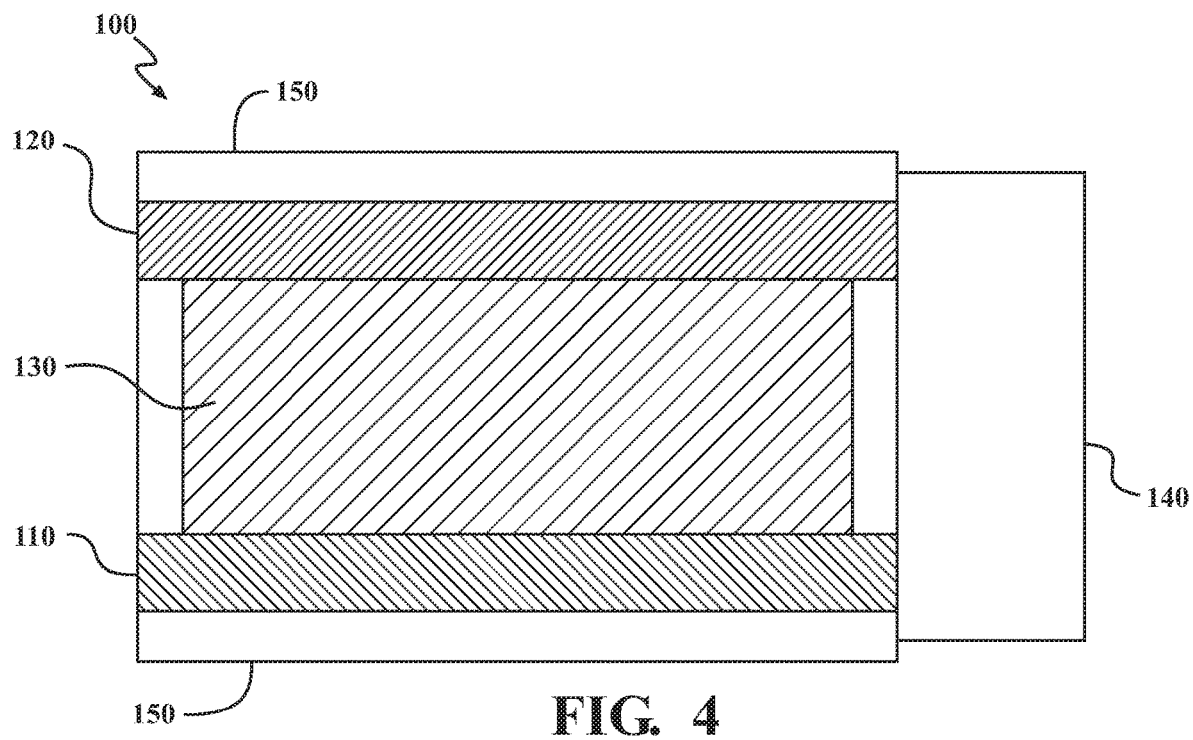
FIG. 4 is a schematic illustration of an electrochemical cell having an ionic liquid that includes a cation of the type shown in FIGS. 1A and 1B, and an anion of the type shown in FIGS. 2A-2C.

An electrochemical cell 100 is also disclosed, as shown in FIG. 4. The electrochemical cell 100 has an anode 110, a cathode 120, and an electrolyte 130 that includes the disclosed ionic liquid and mediates ionic communication between the anode 110 and the cathode 120. The electrochemical cell can also include an external conductor 140 that mediates electric communication between the anode 110 and the cathode 120. In the case of the example of FIG. 4, the external conductor 140 connects current collectors 150. In some implementations, the electrochemical cell can be a Faradaic pseudocapacitor. In many implementations, the electrochemical cell 100 will be a secondary voltaic cell, mediating reversible oxidation/reduction of an active material, M, in the storage and release of electric power.

In various implementations, the active material can include one or more of magnesium, lithium, sodium, potassium, zinc, calcium, ionic insertion materials such as those based on carbonaceous materials or oxides such as titanates, an organic active material. Suitable examples of organic active materials include, without limitation, quinones and quinone derivatives, (2,2,6,6-tetramethyl-piperidin-1-yl) oxyl (TEMPO) and other nitroxy organic molecules, and alkoxybenzenes. In some specific implementations, the active material will include magnesium or lithium.

Active material is oxidized during discharge of the electrochemical cell 100 at the anode 110 during cell discharge, and is reduced at the anode 110 during cell charging according to Reaction I:

$$M \rightarrow M^+ + e^- \qquad \text{I.}$$

Thus, the anode will contain reduced active material when at least partially charged. While the generic example of Reaction I shows an atom of an active metal oxidized to a monovalent cation, having a +1 charge, and a single electron, it will be appreciated that, depending on the identity of an active metal, a single oxidation event can produce a divalent or polyvalent cation and more than one electron. Alternatively, an organic active material may not acquire a charge when oxidized. In instances where the active material is a metal/metal cation, the anode can be composed of the metal. In other such instances, the anode can be made of a different metal, such as a tin insertion anode for insertion of magnesium in a magnesium cell. In some instances, the anode can be an intercalation material, such as graphite, or a transition metal dichalcogenide.

Figure 5:
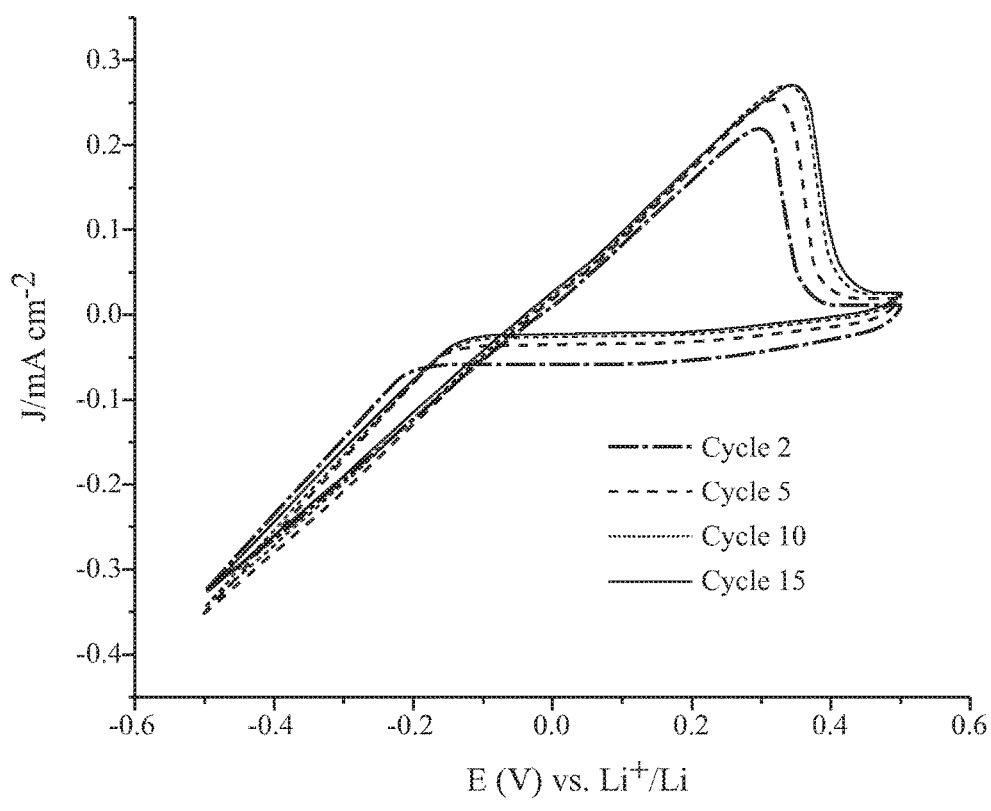
FIG. 5 is a cyclic voltammogram, showing multiple non-sequential lithium stripping/deposition cycles of a 3-electrode Li-ion cell of the type shown generically in FIG. 4.

As stated above, the electrolyte 130 includes the disclosed ionic liquid described above. The electrolyte 130 can also include an ionic shuttle salt, to improve the transport of active material between the anode 110 and the cathode 120. In many such implementations, the shuttle sale will have include an oxidized form of the active material as cation. For example, in implementations where the electrochemical cell is a Li-ion cell, the electrolyte 130 can include LiTFSI, or any other ionic shuttle salt suitable for a Li-ion cell. Similarly, in implementations where the electrochemical cell is a magnesium cell, the electrolyte 130 can include Mg[CB$_{11}$H$_{12}$]$_2$, or any other ionic shuttle salt suitable for a magnesium cell. In some implementations, the electrolyte can also include a co-solvent in admixture with the ionic liquid. Such a co-solvent can optionally be employed to improve the conductivity of the electrolyte 130, such as by increasing the solubility of an ionic shuttle salt in the electrolyte 130, lowering the viscosity of the electrolyte 130, or both. Non-limiting examples of suitable co-solvents include: solvents that can coordinate metal cations as polydentate ligands, such as glymes or other polyethers; polar but non-coordinating or weakly coordinating solvents, such as tetrahydrofuran; or non-polar, non-coordinating solvents, such as toluene. FIG. 5 shows four cycles of cyclic voltammetry for a Li-ion cell having an electrolyte of 0.2M LiTFSI in [N$_{4(2O2O1)(2O2O1)(2O2O1)}$][CB$_{11}$H$_{12}$], a nickel working electrode, and a lithium counter electrode. The results show that the cell undergoes stable cycling for multiple cycles across a fairly broad electric potential window.

The cathode 120 can be composed of any material suitable to the electrochemistry of the cell 100, and having appropriate redox potential relative to the anode 110. Suitable but non-exclusive examples of such materials can include a Chevrel phase molybdenum composition such as Mo$_6$S$_8$, FeSiO$_4$, K-αMnO$_2$, FePO$_4$, Cu$_2$V$_2$O$_7$, TiS$_4$, NbS$_5$, Li terephthalate, silicon, graphite, sulfur, organosulfur compounds, air, oxygen, or any other suitable materials.

A method for synthesizing an ionic liquid is also disclosed. The ionic liquid is as described above. The disclosed method includes a step of contacting a quaternary salt with a boron cluster salt to produce the ionic liquid via a salt metathesis reaction. The quaternary salt has: a quaternary cation as described above, and a suitable anion. Thus, the quaternary salt can be considered to have a formula AZ, where A is an ammonium or phosphonium cation as disclosed, and Z is an anion. The boron cluster salt has a boron cluster anion, as described above, and an associated cation. The associated cation will typically be an alkali metal cation, but could potentially be another cation, including a complex cation, or a mixture of cations. The stoichiometry of the metathesis reaction will vary depending on the exact species used, but in variations where the associated cation has a +1 charge, will proceed according to Reaction II:

$$M_pQ + pAZ \rightarrow pMZ + A_pQ \qquad \text{II,}$$

wherein M is the associated cation, and A, Q, Z, and p are as defined above. In such implementations, where the associated cation, M, has +1 charge, p will be two when the boron cluster anion has charge −2, and p will be one when the boron cluster anion has charge −1. For example, the metathesis reaction could proceed according to Reactions III or IV:

$$Cs_2[B_{12}H_{12}] + 2[N_{2(2O2O1)(2O2O1)(2O2O1)}]Br \rightarrow 2CsBr + [N_{2(2O2O1)(2O2O1)(2O2O1)}]_2[B_{12}H_{12}] \qquad \text{III,}$$

$$Cs[CB_{11}H_{12}] + [N_{4(2O2O1)(2O2O1)(2O2O1)}]Br \rightarrow CsBr + [N_{4(2O2O1)(2O2O1)(2O2O1)}][CB_{11}H_{12}] \qquad \text{IV.}$$

It will be readily understood that the metathesis forms a salt of the halide and the associated cation as a side product.

The method for synthesizing an ionic liquid can further include a step of isolating the newly synthesized ionic liquid. In many implementations, the step of contacting a quaternary salt with a boron cluster salt (hereinafter referred to alternatively as "the metathesis") can be performed in a metathesis solvent in which the reactants and the side product are soluble, but in which the ionic liquid product is substantially insoluble and/or immiscible, such as having a solubility less than 0.01 M, or less than 0.001 M. Thus, when the metathesis is performed at a temperature below the melting temperature of the ionic liquid, the ionic liquid product will form an insoluble, solid precipitate; and when the metathesis is performed at a temperature above the melting temperature of the ionic liquid, the ionic liquid product will form as a separate, immiscible liquid layer. In implementations where the ionic liquid forms as an insoluble solid, the step of isolating the newly synthesized ionic liquid can be easily performed, for example by filtration or by centrifugation and decanting. In implementations where the ionic liquid forms as an immiscible liquid layer, the step of isolating the ionic liquid can be performed by solvent extraction, with an extraction solvent such as dichloromethane. Solvents metathesis suitable in which the ionic liquid can form as a solid precipitate or as an immiscible liquid layer can, in various implementations, include water, methanol, ethanol, and a mixture thereof.

The method for synthesizing an ionic liquid can further include a step of purifying the isolated ionic liquid. In various implementations, the step of purifying the isolated ionic liquid can be performed by: contacting the isolated ionic liquid with a solid adsorbent, such as activated alumina, silica, or activated charcoal; contacting the isolated ionic liquid with a highly water-reactive metal, such as lithium metal or magnesium shavings; heating the isolated ionic liquid at temperatures up to 100° C. under vacuum; and any combination of the above methods. The step of purifying the isolated ionic liquid can be conducted in the presence of a co-solvent that is miscible with the ionic liquid, such as dichloromethane or toluene.

Figure 6A:
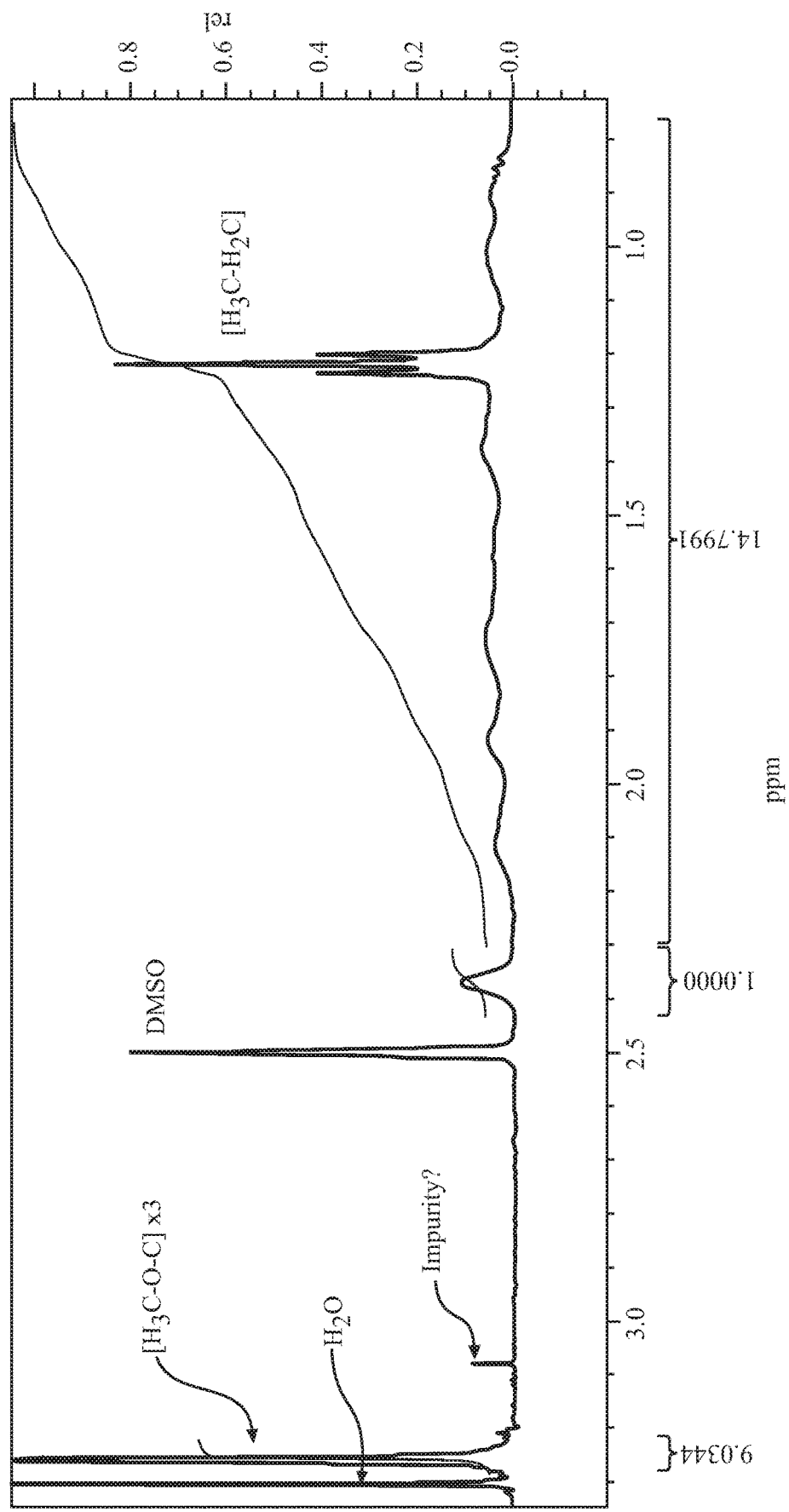
FIG. 6A is a proton nuclear magnetic resonance (NMR) spectrum of an unpurified ionic liquid of the present disclosure.
Figure 6B:
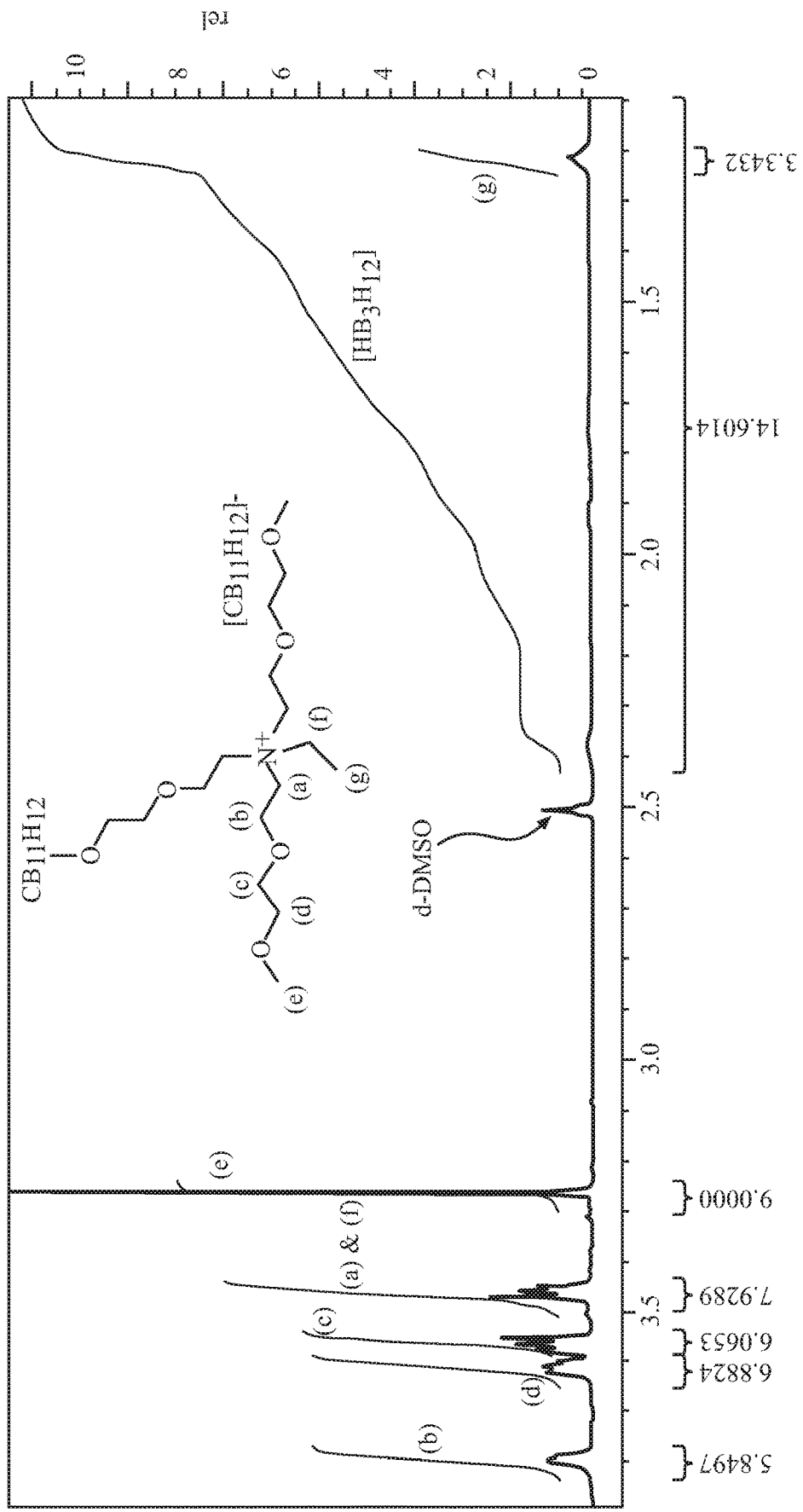
FIG. 6B is a proton NMR spectrum of a purified ionic liquid of the present disclosure, N-ethyl-N,N,N-tris[2-(2-methoxyethoxy)ethyl]ammonium carba-closo-dodecaborate $[N_{2(2O2O1)(2O2O1)(2O2O1)}][CB_{11}H_{12}]$.
Figure 6C:
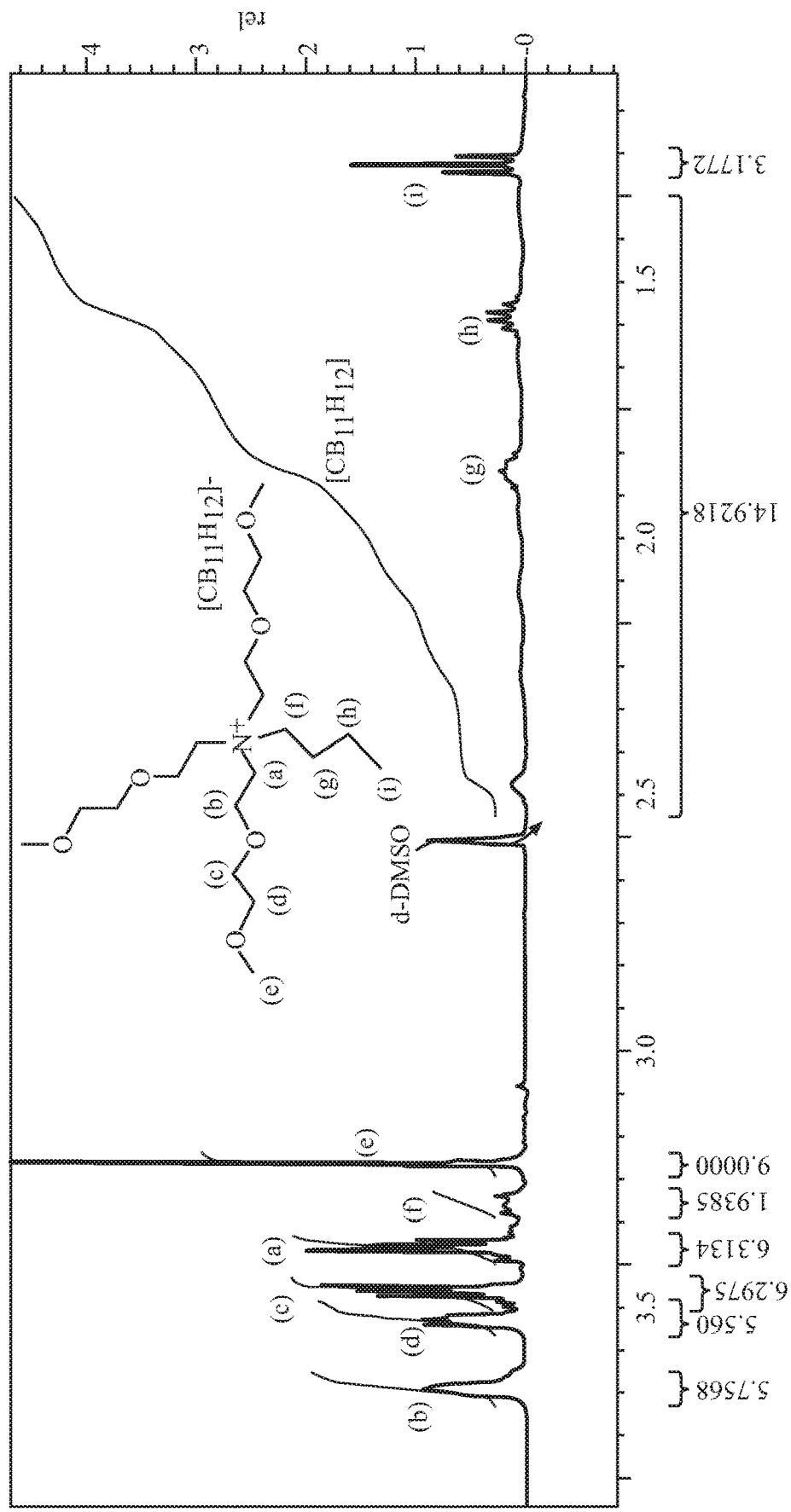
FIG. 6C is a proton NMR spectrum of a purified ionic liquid of the present disclosure, N-butyl-N,N,N-tris [2-(2-methoxyethoxy)ethyl]ammonium carba-closo-dodecaborate $[N_{4(2O2O1)(2O2O1)(2O2O1)}][CB_{11}H_{12}]$.

FIG. 6A shows a $^1$H NMR spectrum of a disclosed ionic liquid that is isolated from the metathesis reaction mixture, but which has undergone no additional purification. Protons from the boron cluster anion and C—H protons from the ammonium side chain arms are labeled. Dimethylsulfoxide is added as a measurement reference. As can be seen from FIG. 6A the ionic liquid that is synthesized and extracted, but has undergone no additional purification, retains substantial water from the metathesis reaction mixture. It will thus be appreciated that purification will likely be preferred for applications where the presence of trace water could be detrimental, such as many electrochemical applications. FIGS. 6B and 6C show $^1$H NMR spectra of $[N_{2(2O2O1)(2O2O1)(2O2O1)}][CB_{11}H_{12}]$ and $[N_{4(2O2O1)(2O2O1)(2O2O1)}][CB_{11}H_{12}]$, respectively, synthesized according to the disclosed method, including the step of purifying the isolated ionic liquid. The NMR spectra of FIGS. 6B and 6C confirm that the purified ionic liquids are substantially dry, and suitable for use in applications in which trace water could be detrimental.

Figure 7:
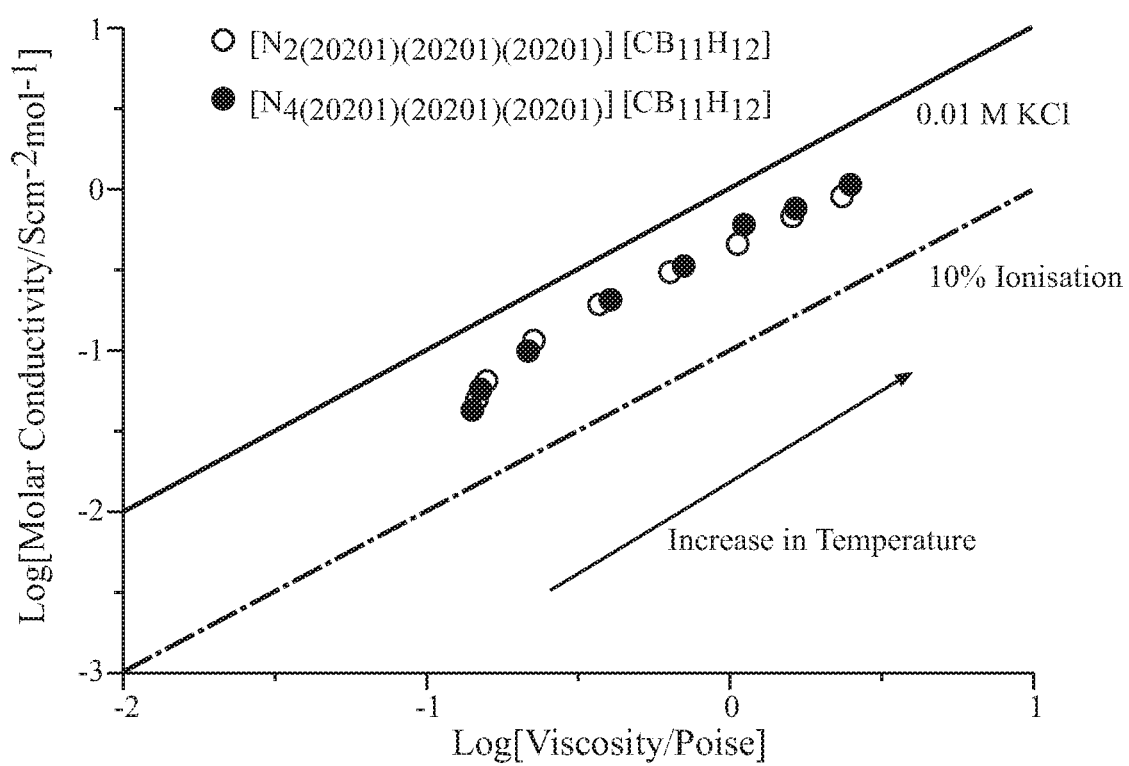
FIG. 7 is a Walden plot, showing the logarithm of molar conductivity as a function of the logarithm of viscosity, for the ionic liquids of FIGS. 6B and 6C.

The ionic liquids of FIGS. 6B and 6C have good dissociation properties as determined by the Walden Plot shown in FIG. 7, a log-log plot of molar conductivity (Λ) vs. viscosity (η) indicating the degree of ionicity of the exemplary ionic liquids. The disclosed ionic liquids show good linearity, with ionization substantially greater than 10%, and near to that of the 'ideal' case of completely dissociated 0.01M KCl.

The present invention is further illustrated with respect to the following examples. It needs to be understood that these examples are provided to illustrate specific embodiments of the present invention and should not be construed as limiting the scope of the present invention.

Examples. Synthesis of Ionic Liquid

In both instances, the quaternary salt $[N_{2(2O2O1)(2O2O1)(2O2O1)}]Br$ and $[N_{4(2O2O1)(2O2O1)(2O2O1)}]Br$, respectively is contacted with $CsCB_{11}H_{12}$ in water for 12 hrs. The ensuing metathesis results in the formation of water-insoluble $[N_{2(2O2O1)(2O2O1)(2O2O1)}][CB_{11}H_{12}]$ or $[N_{4(2O2O1)(2O2O1)(2O2O1)}][CB_{11}H_{12}]$, respectively, and CsBr in solution. The newly synthesized ionic liquid is purified by extraction with dichloromethane, followed by contacting with charcoal and activated alumina, using dichloromethane as an eluent.

The preceding description is merely illustrative in nature and is in no way intended to limit the disclosure, its application, or uses. As used herein, the phrase at least one of A, B, and C should be construed to mean a logical (A or B or C), using a non-exclusive logical "or." It should be understood that the various steps within a method may be executed in different order without altering the principles of the present disclosure. Disclosure of ranges includes disclosure of all ranges and subdivided ranges within the entire range.

The headings (such as "Background" and "Summary") and sub-headings used herein are intended only for general organization of topics within the present disclosure, and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment or particular system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

What is claimed is:

1. A method for synthesizing an ionic liquid, the method comprising:
   contacting a quaternary salt with a boron cluster salt in a metathesis solvent in which the ionic liquid is insoluble at a temperature above a melting temperature of the ionic liquid to form the ionic liquid via a salt metathesis reaction and as an immiscible liquid layer, the quaternary salt comprising a quaternary cation comprising at least one of:

an ammonium cation having a structure:

and a phosphonium cation having a structure:

wherein $R_1$, $R_2$, $R_3$, and $R_4$ is each, independently, selected from a group consisting of:
- C2-C12 alkyl; and
- poly(ethylene glycol) methyl ether having from 1-20 ethylene glycol subunits.

2. The method as recited in claim 1, wherein the boron cluster salt comprises an alkali metal cation.

3. The method as recited in claim 1, wherein the boron cluster salt comprises a boron cluster anion having a formula $[B_yH_{(y-z-i)}R_zX_i]^{2-}$, $[CB_{(y-1)}H_{(y-z-i)}R_zX_i]^-$, $[C_2B_{(y-2)}H_{(y-t-j-1)}R_tX_j]^-$, $[C_2B_{(y-3)}H_{(y-t-j)}R_tX_j]^-$, or $[C_2B_{(y-3)}H_{(y-t-j-1)}R_tX_j]^{2-}$, and wherein:
- y is an integer within a range of 6 to 12;
- (z+i) is an integer within a range of 0 to y;
- (t+j) is an integer within a range of 0 to (y-1);
- X is F, Cl, Br, I, or a combination thereof; and
- R is a substituent comprising any of:
  - group (i): a linear, branched-chain, or cyclic C1-C18 alkyl, perfluoroalkyl, or partially fluorinated alkyl group;
  - group (ii): a C6-C14 aryl, perfluoroaryl, or partially fluorinated aryl group;
  - group (iii): a linear, branched-chain, or cyclic C1-C18 alkoxy, perfluoroalkoxy, or partially fluorinated alkoxy group;
  - group (iv): a C6-C14 aryloxy, perfluoroaryloxy, or partially fluorinated aryloxy group; and
  - group (v): a substituent that combines moieties defined by two or more of groups (i)-(iv).

4. The method as recited in claim 1, wherein the boron cluster salt comprises at least one boron cluster anion selected from a group consisting of closo-$[B_{12}H_{12}]^{2-}$, closo-$[CB_{11}H_{12}]^-$, and closo-$[C_2B_{10}H_{11}]^-$.

5. The method as recited in claim 1, further comprising extracting the immiscible liquid layer with a solvent in which the immiscible liquid layer is soluble.

6. The method as recited in claim 1, further comprising purifying the ionic liquid by a procedure selected from a group consisting of:
- contacting the ionic liquid with an adsorbent;
- contacting the ionic liquid with a highly water-reactive metal; and
- placing the ionic liquid under vacuum at a temperature up to 100° C.

7. A method for synthesizing an ionic liquid, the method comprising:

contacting a quaternary salt with a boron cluster salt comprising an alkali metal cation in a metathesis solvent in which the ionic liquid is insoluble at a temperature above a melting temperature of the ionic liquid to form the ionic liquid via a salt metathesis reaction and as an immiscible liquid layer, the quaternary salt comprising a quaternary cation comprising at least one of:

an ammonium cation having a structure:

and a phosphonium cation having a structure:

wherein $R_1$, $R_2$, $R_3$, and $R_4$ is each, independently, selected from a group consisting of:
- C2-C12 alkyl; and
- poly(ethylene glycol) methyl ether having from 1-20 ethylene glycol subunits.

8. The method as recited in claim 7, wherein the boron cluster salt comprises a boron cluster anion having a formula $[B_yH_{(y-z-i)}R_zX_i]^{2-}$, $[CB_{(y-1)}H_{(y-z-i)}R_zX_i]^-$, $[C_2B_{(y-2)}H_{(y-t-j-1)}R_tX_j]^-$, $[C_2B_{(y-3)}H_{(y-t-j)}R_tX_j]^-$, or $[C_2B_{(y-3)}H_{(y-t-j-1)}R_tX_j]^{2-}$, and wherein:
- y is an integer within a range of 6 to 12;
- (z+i) is an integer within a range of 0 to y;
- (t+j) is an integer within a range of 0 to (y-1);
- X is F, Cl, Br, I, or a combination thereof; and
- R is a substituent comprising any of:
  - group (i): a linear, branched-chain, or cyclic C1-C18 alkyl, perfluoroalkyl, or partially fluorinated alkyl group;
  - group (ii): a C6-C14 aryl, perfluoroaryl, or partially fluorinated aryl group;
  - group (iii): a linear, branched-chain, or cyclic C1-C18 alkoxy, perfluoroalkoxy, or partially fluorinated alkoxy group;
  - group (iv): a C6-C14 aryloxy, perfluoroaryloxy, or partially fluorinated aryloxy group; and
  - group (v): a substituent that combines moieties defined by two or more of groups (i)-(iv).

9. The method as recited in claim 7, wherein the boron cluster salt comprises at least one boron cluster anion selected from a group consisting of closo-$[B_{12}H_{12}]^{2-}$, closo-$[CB_{11}H_{12}]^-$, and closo-$[C_2B_{10}H_{11}]^-$.

10. The method as recited in claim 7, further comprising extracting the immiscible liquid layer with a solvent in which the immiscible liquid layer is soluble.

11. The method as recited in claim 7, further comprising purifying the ionic liquid by a procedure selected from a group consisting of:
- contacting the ionic liquid with an adsorbent;
- contacting the ionic liquid with a highly water-reactive metal; and placing the ionic liquid under vacuum at a temperature up to 100° C.

12. A method for synthesizing an ionic liquid, the method comprising:

contacting a quaternary salt with a boron cluster salt in a metathesis solvent in which the ionic liquid is insoluble at a temperature above a melting temperature of the ionic liquid to form the ionic liquid via a salt metathesis reaction and as an immiscible liquid layer, the quaternary salt comprising a quaternary cation comprising at least one of:

an ammonium cation having a structure:

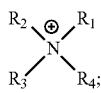

and a phosphonium cation having a structure:

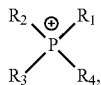

wherein $R_1$, $R_2$, $R_3$, and $R_4$ is each, independently, selected from a group consisting of:

C2-C12 alkyl; and poly(ethylene glycol) methyl ether having from 1-20 ethylene glycol subunits; and extracting the immiscible liquid layer with a solvent in which the immiscible liquid layer is soluble.

13. The method as recited in claim 12, wherein the boron cluster salt comprises an alkali metal cation.

14. The method as recited in claim 12, wherein the boron cluster salt comprises a boron cluster anion having a formula $[B_yH_{(y-z-i)}R_zX_i]^{2-}$, $[CB_{(y-1)}H_{(y-z-i)}R_zX_i]^-$, $[C_2B_{(y-2)}H_{(y-t-j-1)}R_tX_j]^-$, $[C_2B_{(y-3)}H_{(y-t-j)}R_tX_j]^-$, or $[C_2B_{(y-3)}H_{(y-t-j-1)}R_tX_j]^{2-}$, and wherein:

y is an integer within a range of 6 to 12;

(z+i) is an integer within a range of 0 to y;

(t+j) is an integer within a range of 0 to (y-1);

X is F, Cl, Br, I, or a combination thereof; and

R is a substituent comprising any of:

group (i): a linear, branched-chain, or cyclic C1-C18 alkyl, perfluoroalkyl, or partially fluorinated alkyl group;

group (ii): a C6-C14 aryl, perfluoroaryl, or partially fluorinated aryl group;

group (iii): a linear, branched-chain, or cyclic C1-C18 alkoxy, perfluoroalkoxy, or partially fluorinated alkoxy group;

group (iv): a C6-C14 aryloxy, perfluoroaryloxy, or partially fluorinated aryloxy group; and group (v): a substituent that combines moieties defined by two or more of groups (i)-(iv).

15. The method as recited in claim 12, wherein the boron cluster salt comprises at least one boron cluster anion selected from a group consisting of closo-$[B_{12}H_{12}]^{2-}$, closo-$[CB_{11}H_{12}]^-$, and closo-$[C_2B_{10}H_{11}]^-$.

16. The method as recited in claim 12, further comprising purifying the ionic liquid by a procedure selected from a group consisting of:

contacting the ionic liquid with an adsorbent;

contacting the ionic liquid with a highly water-reactive metal; and placing the ionic liquid under vacuum at a temperature up to 100° C.

* * * * *